United States Patent [19]

Green

[11] Patent Number: 4,518,356

[45] Date of Patent: May 21, 1985

[54] UTRASONIC DENTAL FILE AND METHOD OF DETERMINING FAILURE RESISTANT LENGTHS THEREOF

[75] Inventor: Russell D. Green, Georgetown, Del.

[73] Assignee: Dentsply Research & Development Corp., Milford, Del.

[21] Appl. No.: 537,890

[22] Filed: Sep. 30, 1983

[51] Int. Cl.³ .............................................. A61C 5/02
[52] U.S. Cl. .................................... 433/102; 433/166
[58] Field of Search ........................ 433/224, 102, 166

[56] References Cited

U.S. PATENT DOCUMENTS

| | | | |
|---|---|---|---|
| 4,190,958 | 3/1980 | Martin | 433/102 |
| 4,229,168 | 10/1980 | Scholz | 433/102 |
| 4,299,571 | 11/1981 | McSpadden . | |
| 4,330,278 | 5/1982 | Martin . | |
| 4,332,561 | 6/1982 | McSpadden . | |

FOREIGN PATENT DOCUMENTS

0019356A1 10/1980 European Pat. Off. .
WO79/00344 6/1979 PCT Int'l Appl. .

OTHER PUBLICATIONS

*Die Quintessenz*, No. 3, Mar. 1973, Berlin; J. M. Laurichesse et al., "Normen von Wurzelkanalinstrumenten", pp. 31–34.

Primary Examiner—Robert Peshock
Attorney, Agent, or Firm—C. Hercus Just; Edward J. Hanson, Jr.

[57] ABSTRACT

An ultrasonic endodontic file that is resistant to failure from fracturing and breaking during operation by having an ideal length, which if increased or decreased by more than 1 mm, will result in increased file breakage.

3 Claims, 2 Drawing Figures

UTRASONIC DENTAL FILE AND METHOD OF DETERMINING FAILURE RESISTANT LENGTHS THEREOF

BACKGROUND OF THE INVENTION

This invention relates to the field of endodontic dentistry and, in particular, to the adaptation of ultrasonics thereto and specifically to ultrasonic endodontic files.

The concept of using ultrasonic instruments in the field of endodontia is known as shown by U.S. Pat. No. 4,330,278. Files for such use are also known as illustrated in the aforementioned U.S. Pat. No. 4,330,278. Other patents refer to files used in powered instruments for endodontia, for example, U.S. Pat. No. 4,299,571. In addition to the files described in the previously referred to patents, the K file which is of square cross-section and axially twisted during manufacture and other endodontic file configurations are discussed in European Patent Application No. 0 019 356A1, published Nov. 26, 1980.

From before June 30, 1980 which is the filing date of U.S. Pat. No. 4,330,278, research effort has been devoted to making ultrasonic endodontia commercially feasible rather than just an experimental undertaking. It is believed that only now with the final step of the invention of the present application has really practical ultrasonic instrumentation of endodontic files become possible.

An object of the present invention is to provide endodontic files having practical utility in ultrasonic instruments.

It is a further object to provide such files within the confines of the basic concepts of commercially available endodontic file construction.

SUMMARY OF THE INVENTION

By the present invention, ultrasonic endodontic files are provided that are resistant to failure by fracture or breaking. The invention depends upon an empirical discovery that does not appear to follow the various hypothesized theories of expectation. For example, the files of Example 3 do not break at the point of greatest flexing movement at a nodal point during ultrasonic operation. The files of Example 1 appear to fail or break at the point of greatest flexing movement and originally suggested a basic hypothesis that did not prove out. Therefore, the invention is claimed in terms of what works as determined empirically once the possibility of empirical determination of ultrasonic endodontic file construction parameters was understood.

Depending on the specific nature of the ultrasonic endodontic file, the determination is that the empirically determined length of the file cannot be departed from by more than 1 mm or in more rigorous circumstances 0.5 mm or 0.25 mm.

DESCRIPTION OF THE PREFERRED EMBODIMENT

The present invention in its preferred embodiment is an ultrasonic endodontic file having a length that when subjected to ultrasonic vibration resists failure compared to an endodontic file of identical parameters except for dimensional length which is varied ±1 mm. Preferably, in more extreme conditions, the rate of increased failure will not change materially unless the length is varied more than ±0.5 mm and in very extreme conditions a material increase in the failure rate may be evident if the length is varied more than ±0.25 mm.

The ultrasonic endodontic file's failure is registered by fracture, breaking at the fracture or breaking straight away. The test for this failure is to take the file and connect it to a standard ultrasonic endodontic capable dental instrument mounted stationarily. Files varying in length by increments of 0.25 mm are prepared in a test spectrum of 1.5 mm to each side of the file being tested in replications of 10 each. Breakage is tested in groups of 10 replications, as a defective instrument is always a possibility. Obviously, the files in the test must have identical material and dimensional parameters except for their lengths. The test is carried out with the files submerged in water to within 2 mm of their engagement with and restrained by the ultrasonic handpiece. They are each operated through 8 cycles of 2 minutes on and 2 minutes off. By observing and recording failures, it is quickly apparent when the limitations of this test are met. The fractures and breaking are determined by visual observation with the naked eye. The standard ultrasonic endodontic capable dental instrument will, is anticipated, vary over the years and, in fact, there may in time be a number of variant standard ultrasonic endodontic capable dental instruments available at the same time. Different files may have to be made for different variant standard ultrasonic endodontic capable dental instruments and thus the test only needs to be validated with the instrument or instruments for which a given file is to be used.

Figure 1:
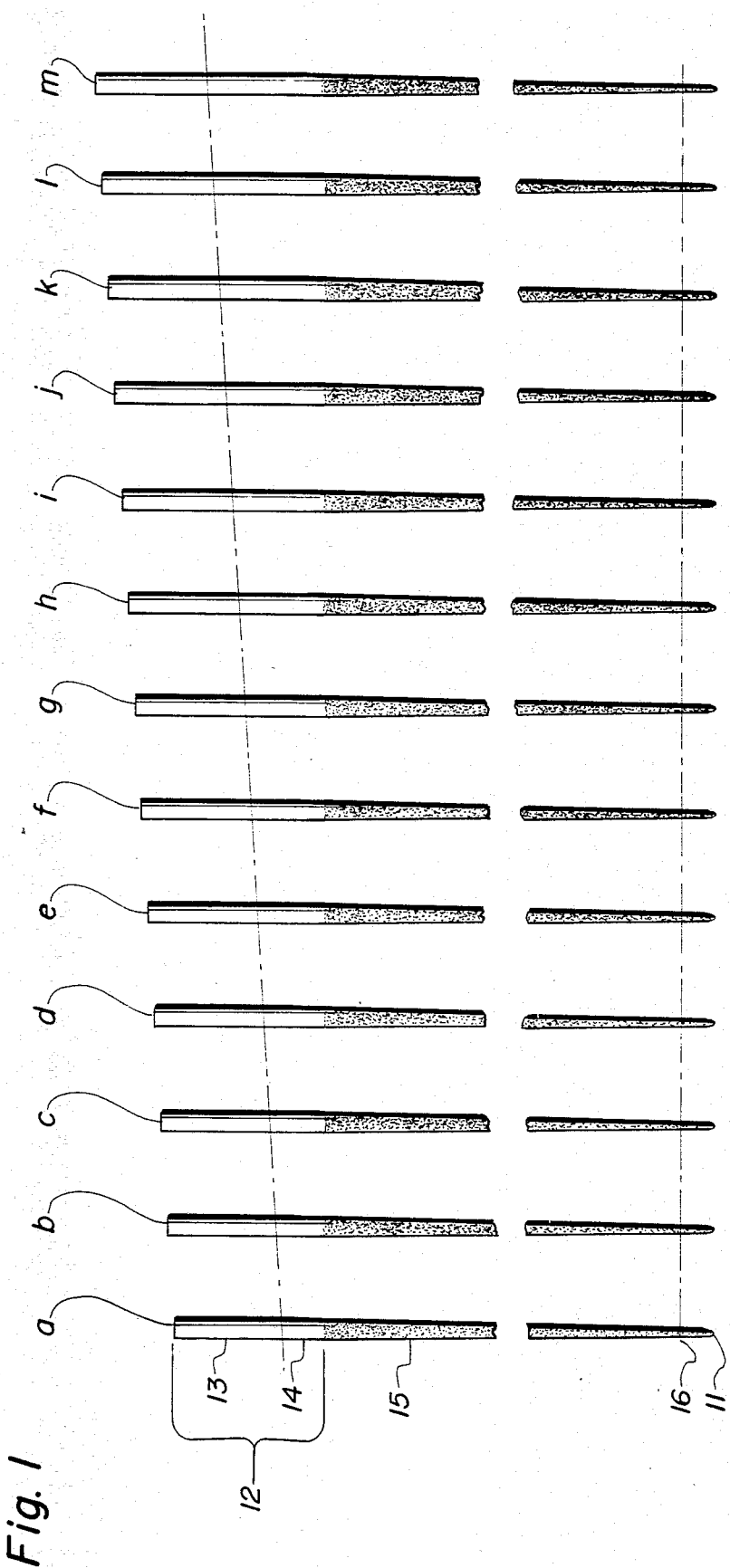
FIG. 1 is a theoretical schematic view of a series of files, roughly four times the usual size of a typical file.

Looking at FIG. 1, an array of 13 files, a through m, is shown such as would be subjected to test in replications of 10 each to determine the position of a file within or without the limits of the present invention. The "size" or thickness of the file often referred to in endodontics as the file "number" is measured 1 mm from the tip of the file which is the end opposite the shank.

Referring to file a in FIG. 1, for purposes of designating the parts of a file, tip 11 of file a may be seen opposite the shank 12 end of the file. The shank 12 has two portions, an outer portion 13 which is engaged by the chuck of ultrasonic handpiece (shown in phantom lines in FIG. 2) and a portion 14 extending to the tapered portion 15 of the file, the tapered part of file a is the portion that is provided with a working surface. As shown, the working surface is of the diamond-nickel plated circular wire type or other diamond-coated type. In the illustration, the working or cutting surface is the full length of the tapered portion, but this is not always the situation. In many instances, the working surface will extend for only a portion of the tapered length. A file also has a working length which is the depth the file may penetrate before the handpiece is engaged with the tooth. This would be the face of the ultrasonic handpiece head shown in FIG. 2. The size or thickness of the file is the greatest cross-sectional thickness of the file measured at phantom line 16 which is 1 mm from the tip 11 of the file.

As shown diagrammatically in FIG. 1, the length of the file in a group being tested is preferably varied by varying the length of the shank 12. To provide a given file of the length required by the present invention, it may be necessary to have a reduced upper or chuck portion length engaged in the chuck or to actually engage a portion of the tapered or mandrel part of the file in the chuck to provide the proper flexing length. By flexing length, it is meant that portion of the file that is not gripped or substantially restrained by the chuck or other parts from flexing or assuming the wave type shape as discussed with respect to FIG. 2. The flexing length and the working length in FIG. 2 are the same, but they would not be the same if, for example, the mouth from the ultrasonic handpiece having the chuck associated with it was an enlarged mouth that would allow the file to flex within the line defined by the outermost face of the head of the handpiece.

Figure 2:
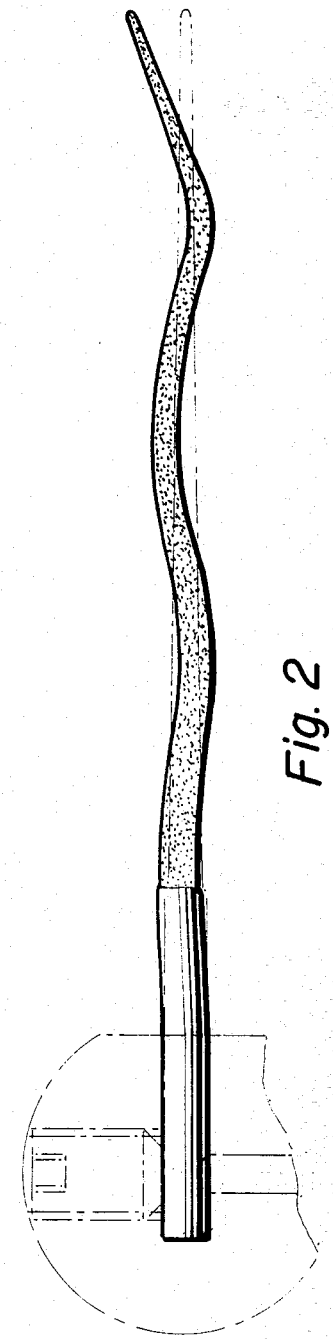
FIG. 2 is a diagramatic representation of how a file flexes.

Looking at FIG. 2, it will be understood that during ultrasonic vibration, the files build up a resonance and tend to flex or bend from one or more given points or nodes. The node nearest to the tip is the one from which a free "waggle" or whipping can occur. This is because all of that portion of the file not held in the chuck can flex and actively become a part of the wave shape shown in FIG. 2.

As used in this application, identical parameters means that all of the parameters of the file, both as to the dimensions and the materials, are the same in so far as manufacturing tolerances would, with general commercial acceptable variations permit, except for the length which is strictly an extention or reduction, as the case may be, of the dimensional progression of the file. Obviously, within manufacturing limits there are minor variations. The term "geometry" as used in this patent application means the cross-sectional shape and magnitude of progression in configuration of the working length of the ultrasonic endodontic file. By magnitude of progression in configuration of the working length, it is meant that on a smaller file there may be some differences in the rate of diminution of diameter from the upper end of working length to the lower end of the working length and in any terminal point or pilot, but the overall general configuration is recognizably similar except for the differences that would not be unexpected when the difference in size is considered within a family of files of different sizes. By family, it is meant files of the same type and character except varying in size.

As a general proposition, ultrasonic endodontic files differ from other endodontic files in manners that are readily apparent. For example, because the non-ultrasonic endodontic files are intended to be rotated, the shank portion is generally configured with a grip providing usage with rotating hand or mechanical instruments as contrasted to the configuration of the present ultrasonic endodontic files which have shanks that are basically plain, although they may have grooves indicating size or the like thereon.

EXAMPLES

The sets of files in the following Examples were prepared using the empirical method of taking substantial numbers of files of various chosen parameters and varying their lengths until a length corresponding to that of the present invention was found using, in general, the procedure previously described in this application as the test procedure except without the recited replications. Instead, various length sizes were run until a length provided by the present invention was found. In these examples, the shank was varied in length and directly joined with the tapered length which was held constant. The tapered length included a working surface equipped for debriding the root canals. The diminution rate of the taper in each file was 0.02 mm per mm of length of the tapered portion excluding the tip which is often rounded or may be equipped with a pilot. All of the actual files in the examples had transverse circumferential grooves at their upper portions or on their shank portion to aid in determining the depth the file penetrated into a tooth.

Example 1

A set of ultrasonic endodontic files of the plain machined circular wire type has been prepared according to the present invention. They have the following characteristics:

| Size | Diameter in mm | Non-Tapered Shank Portion in mm | Flexing Length in mm | Tapered Length in mm | Working Surface in mm |
|---|---|---|---|---|---|
| 15 | 0.15 | 2 | 19 | 21 | 16 |
| 20 | 0.20 | 4 | 21 | 21 | 16 |
| 25 | 0.25 | 5 | 22 | 21 | 16 |

By size in mm (millimeters) as used in this application, it is meant the cross-sectional dimension of the file at its widest point 1 mm from the tip. Each of the ultrasonic endodontic files in the set or family had the same geometry. It will be understood that size 15 had 2 mm of the tapered length engaged in the chuck of the ultrasonic handpiece.

Example 2

A set of ultrasonic endodontic files of the diamond-nickel plated circular wire type has been prepared according to the present invention. They have the following characteristics:

| Size | Diameter in mm | Non-Tapered Shank Portion in mm | Flexing Length in mm | Tapered Length in mm | Working Surface in mm |
|---|---|---|---|---|---|
| 25 | 0.25 | 3 | 23 | 24 | 15 |
| 35 | 0.35 | 4 | 24 | 24 | 15 |
| 45 | 0.45 | 6 | 25 | 23 | 15 |

Each of the ultrasonic endodontic files in the set or family had the same geometry. The 16 mm working surface is not plated for 1 mm adjacent the tip, the unplated 1 mm tip serving the working function of a guide down in the root canal.

Example 3

A set of ultrasonic endodontic files of the K type has been prepared according to the present invention. They have the following characteristics:

| Size | Diameter in mm | Non-Tapered Shank Portion in mm | Flexing Length in mm | Tapered Length in mm | Fluted Length in mm |
|---|---|---|---|---|---|
| 10 | 0.10 | 7 | 23 | 20 | 17 |
| 15 | 0.15 | 9 | 25 | 20 | 17 |
| 20 | 0.20 | 9 | 25 | 20 | 17 |
| 25 | 0.25 | 5 | 21 | 20 | 17 |

Each of the ultrasonic endodontic files in the set or family had the same geometry.

In each of the above examples, 1, 2, and 3, the overall length is the non-tapered length plus the tapered length.

While in accordance with the patent statutes what is at present considered to be the preferred embodiment of the invention has been described, it will be obvious to those skilled in the art that numerous changes and modifications may be made therein without departing from the invention, and it is therefore aimed in the appended claims to cover all such equivalent variations as fall within the true spirit and scope of the invention.

It is claimed:

1. A method of determining the ideal length of an ultrasonic endodontic file to provide maximum resistance to breakage and including a standard tapered flexible working portion of predetermined length connected to one end of a shank of uniform size and shape of cross-sections from a batch of said files having a range of overall lengths and all of similar diameter 1 mm from the tip end of the working portion, said method comprising the steps of:
    (a) individually testing a plurality of said tapered files having a range of lengths of shanks of uniform cross-sectional shapes and sizes within water to simulate conventional endodontic conditions,
    (b) observing a predetermined number of said files of different lengths successively for same known periods of time until breakage of files of certain lengths occur,
    (c) determining the files of lengths which resist breakage among those in which breakage occurred, within a tolerance of ±1 mm and
    (d) standardizing production of files having said length which resists breakage as determined by the foregoing steps.

2. The method according to claim 1 in which the known periods of time are approximately 2 minutes and then rest for 2 minutes, followed by successive test periods and rests for a limited number of sequences not in excess of 8 successions.

3. An endodontic file having an overall length relative to the diameter thereof which is resistant to fracture at ultrasonic speeds as determined by the process set forth in claim 1.

* * * * *